United States Patent
Yau et al.

(10) Patent No.: US 8,113,835 B2
(45) Date of Patent: Feb. 14, 2012

(54) ABUTMENT ASSEMBLY FOR DENTAL IMPLANT

(75) Inventors: Hong-Tzong Yau, Chiayi County (TW); Wen-Chin Chou, Changhua Hsien (TW)

(73) Assignee: Pou Yu Biotechnology Co., Ltd., Changhua (TW)

( * ) Notice: Subject to any disclaimer, the term of this patent is extended or adjusted under 35 U.S.C. 154(b) by 231 days.

(21) Appl. No.: 12/427,465

(22) Filed: Apr. 21, 2009

(65) Prior Publication Data

US 2010/0266985 A1    Oct. 21, 2010

(51) Int. Cl.
*A61C 8/00* (2006.01)

(52) U.S. Cl. .......................... 433/173; 433/174

(58) Field of Classification Search .......... 433/173–176, 433/201.1, 201.12; 264/16, 17, 19
See application file for complete search history.

(56) References Cited

U.S. PATENT DOCUMENTS

| | | | |
|---|---|---|---|
| 5,040,982 A * | 8/1991 | Stefan-Dogar | 433/169 |
| 5,135,395 A * | 8/1992 | Marlin | 433/174 |
| 5,213,500 A * | 5/1993 | Salazar et al. | 433/169 |
| 5,281,140 A * | 1/1994 | Niznick | 433/172 |
| 6,244,867 B1 * | 6/2001 | Aravena et al. | 433/172 |
| 6,283,753 B1 * | 9/2001 | Willoughby | 433/172 |
| 7,104,797 B2 | 9/2006 | Rassoli | |

FOREIGN PATENT DOCUMENTS

| | | |
|---|---|---|
| EP | 1269932 A1 * | 5/2002 |
| JP | 1993-269149 A | 10/1993 |
| JP | 1998509371 A | 9/1998 |
| TW | 200938170 | 9/2009 |

* cited by examiner

*Primary Examiner* — Todd Manahan
*Assistant Examiner* — Yogesh Patel
(74) *Attorney, Agent, or Firm* — Schwabe, Williamson & Wyatt PC

(57) ABSTRACT

An abutment assembly for use with a dental implant unit includes a metal pedestal unit which has a fitting bushing adapted to fittingly engage a tubular fitted wall of an implant member, a ceramic abutment body which has an annular cut-out in a bottom wall thereof to be mounted on the pedestal unit, and a tubular packing member which has a bearing ledge on an inner peripheral surface to be pressed by a bolt member when the bolt member is threadedly engaged with the implant member, and a pressing region on an outer peripheral surface to be brought to intimately abut against a pressed region of an inner tubular wall surface of the abutment wall so as to place the abutment body in a tightened position.

11 Claims, 14 Drawing Sheets

ABUTMENT ASSEMBLY FOR DENTAL IMPLANT

BACKGROUND OF THE INVENTION

1. Field of the Invention

This invention relates to an abutment assembly for a dental implant, more particularly to an abutment assembly for use with a dental implant unit including an implant member and a bolt member.

2. Description of the Related Art

There are currently available various methods and systems of dental implants. One such implant system includes an implant member screwed into a jaw bone of a patient at a location vacated by a missing tooth, and an abutment mounted on the implant member, and having a coping portion that is exposed from the patient's gums for coupling with an artificial tooth or crown. Such conventional dental implants are described in, e.g., U.S. Pat. No. 7,104,797.

Since the abutment is made from a metal material, such as Titanium (Ti), which is less light-transmissible, the abutment may shadow through the artificial tooth or crown, thereby affecting appearance. Therefore, an abutment made from a ceramic material has been proposed. However, the following disadvantages may arise:

1. During a dental implant process, since the space in a vacancy of the missing tooth is limited, and since the abutment must have a lower interface connected to an upper interface of the implant member, the thickness of the lower interface is not sufficient, which may result in breaking of the abutment;

2. Since the abutment made from a ceramic material is harder than the implant member made from a metal material, during mounting and position-adjustment of the abutment on the implant member, the abutment may rub against the implant member to result in undesirable damage to the implant member; and 3. Since the abutment and the implant member are made from different materials, the connection therebetween is not reliable.

SUMMARY OF THE INVENTION

An object of the present invention is to provide an abutment assembly for use with a dental implant unit, in which breaking of an interface of the abutment assembly during a dental implant process, and damage to the dental implant unit during mounting and position-adjustment of the abutment assembly can be prevented. In addition, a reliable connection between the dental implant unit and the abutment assembly can be ensured.

According to this invention, the abutment assembly includes a pedestal unit, an abutment body and a tubular packing member.

The pedestal unit includes a surrounding mount, a tubular post and a fitting bushing. The surrounding mount has upper and lower mount surfaces. The tubular post extends from the upper mount surface upwardly to terminate at a tubular seat surface, and cooperates with the surrounding mount to define an inner tubular abutted surface. The fitting bushing extends from the lower mount surface downwardly, and is adapted to be in fitting engagement with a tubular fitted wall of the implant member.

The abutment body includes coping-side and bottom walls, and has an inner tubular wall surface which extends longitudinally through the coping-side wall and the bottom wall to form a tubular passage region and a tubular pressed region. The bottom wall has an annular cut-out which extends longitudinally into the tubular pressed region, and which extends inwardly and radially through the inner tubular wall surface so as to form a surrounding shoulder abutment that confronts the tubular seat surface.

The tubular packing member has an inner peripheral surface extending longitudinally to define a through bore, and including a proximate peripheral region adapted to provide access to a bolt member, and a distal peripheral region which is configured to form, in cooperation with the proximate peripheral region, a bearing ledge that confronts a force-applying shoulder of the bolt member when the bolt member is brought to threadedly engage the implant member. The tubular packing member has an outer peripheral surface including pressing and abutting regions which are configured to mate with the tubular pressed region and the inner tubular abutted surface, respectively, such that, once the bearing ledge is forced by the force-applying shoulder to place the abutment body in a tightened position, the pressing region is brought to intimately abut against the tubular pressed region to thereby ensure immobility of the abutment body relative to the bolt member.

BRIEF DESCRIPTION OF THE DRAWINGS

Other features and advantages of the present invention will become apparent in the following detailed description of the preferred embodiments of the invention, with reference to the accompanying drawings, in which.

DETAILED DESCRIPTION OF THE PREFERRED EMBODIMENTS

Figure 1:
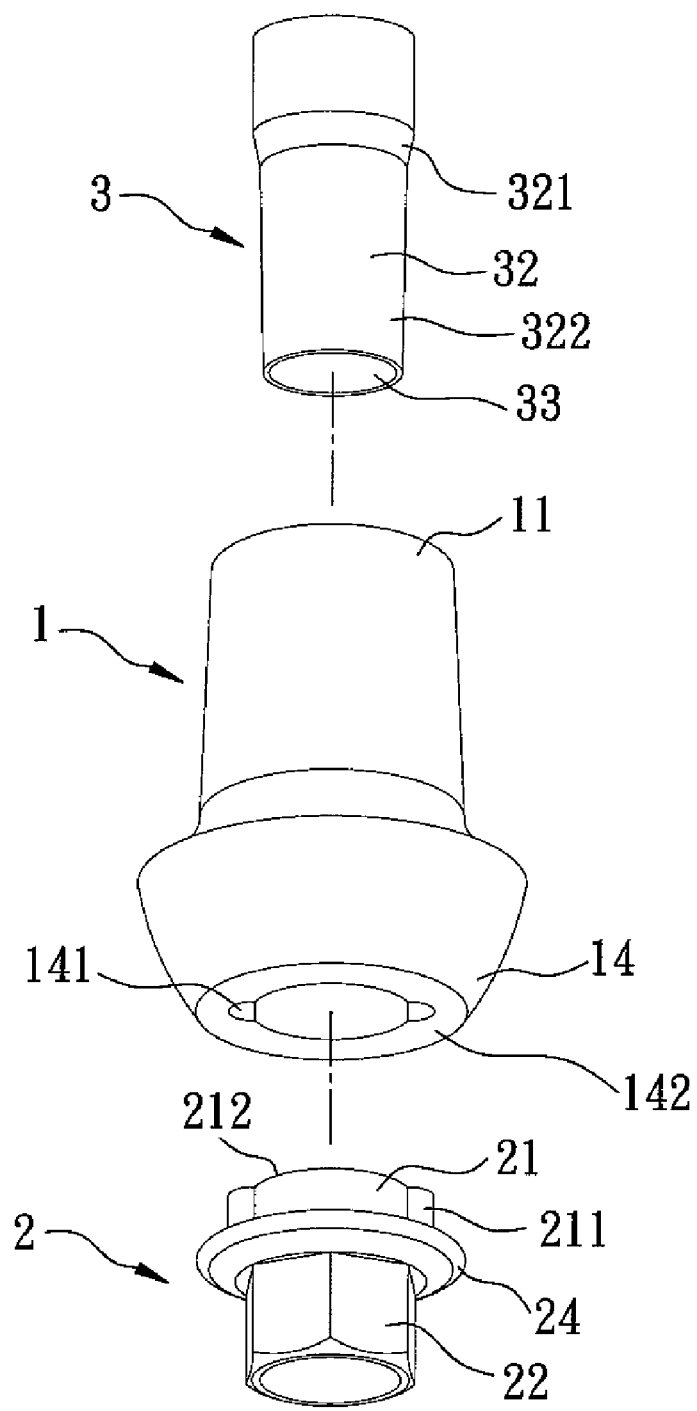
FIG. 1 is an exploded perspective view of the first preferred embodiment of an abutment assembly according to this invention.
Figure 2:
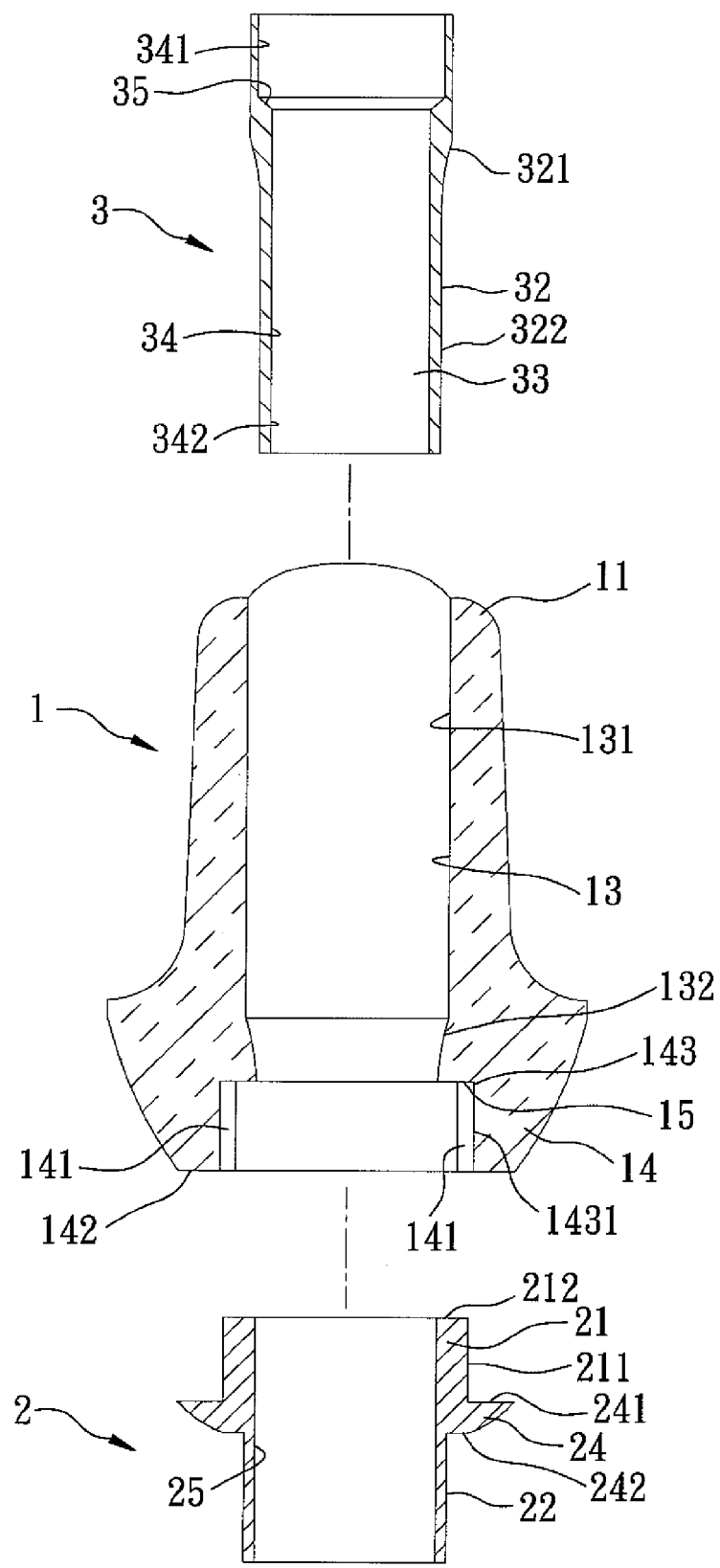
FIG. 2 is an exploded sectional view of the first preferred embodiment.
Figure 3A:
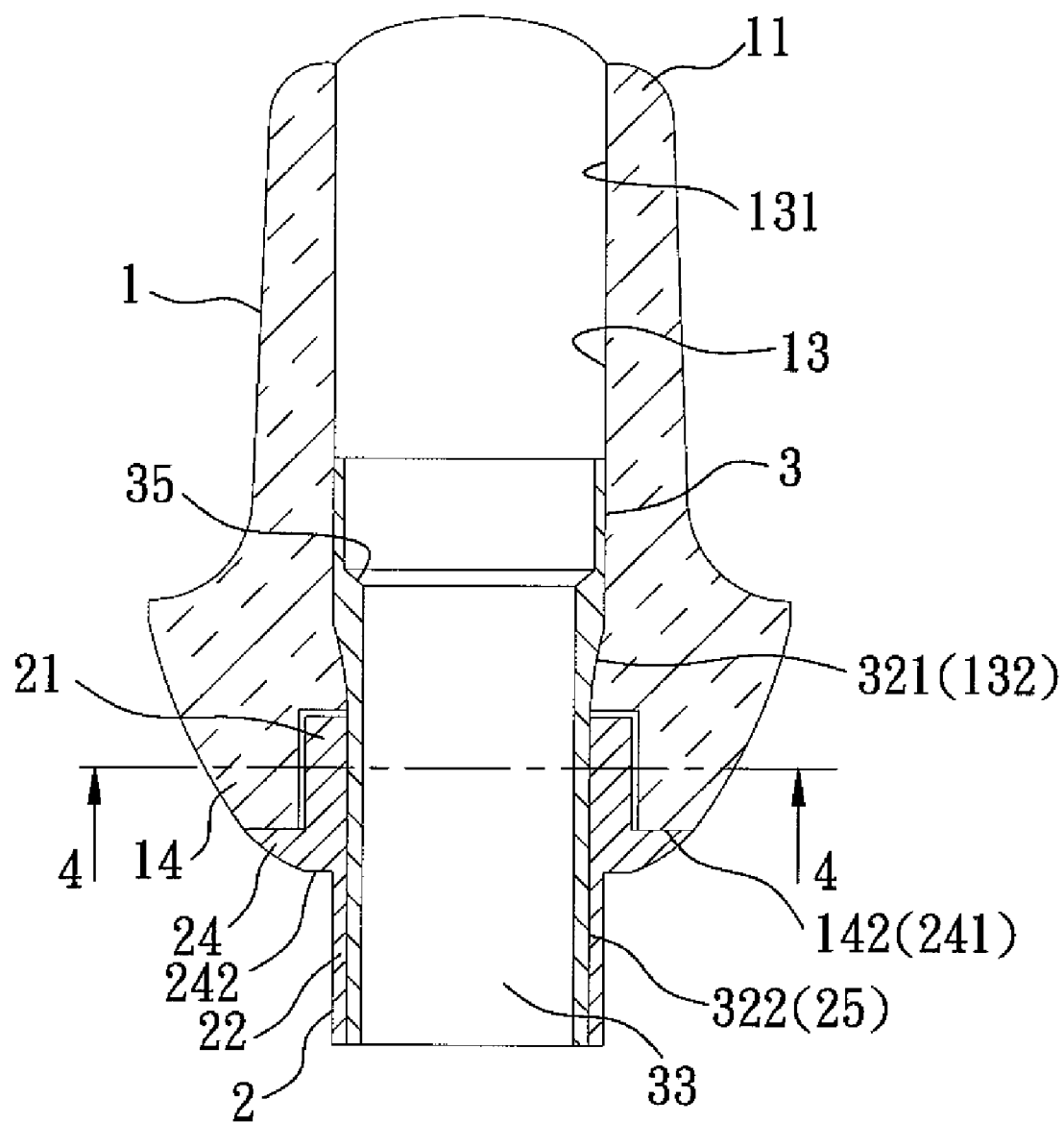
FIG. 3(A) is a sectional view of the first preferred embodiment when assembled.
Figure 3B:
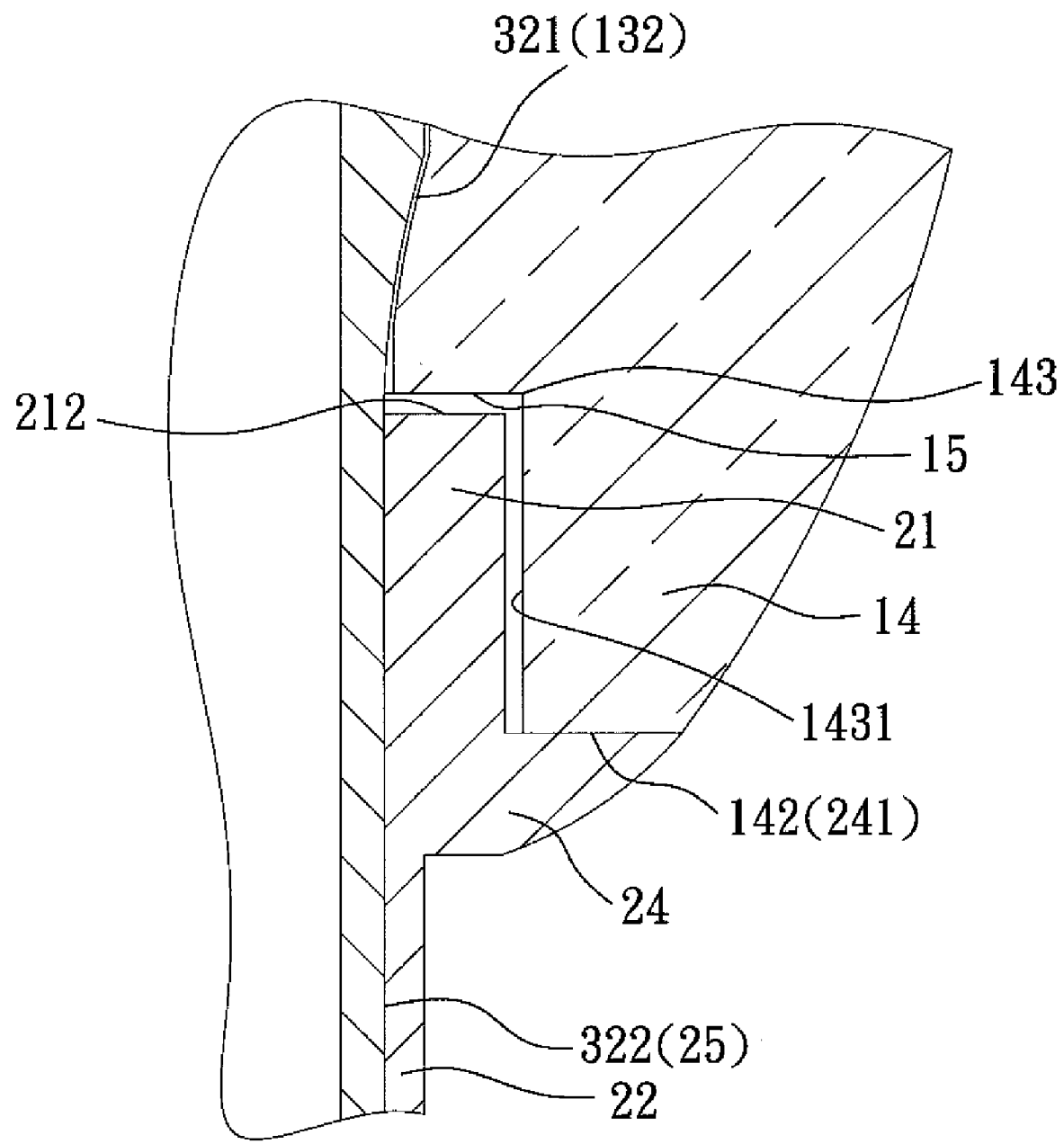
FIG. 3(B) is an enlarged view of a portion in FIG. 3(A)
Figure 4:
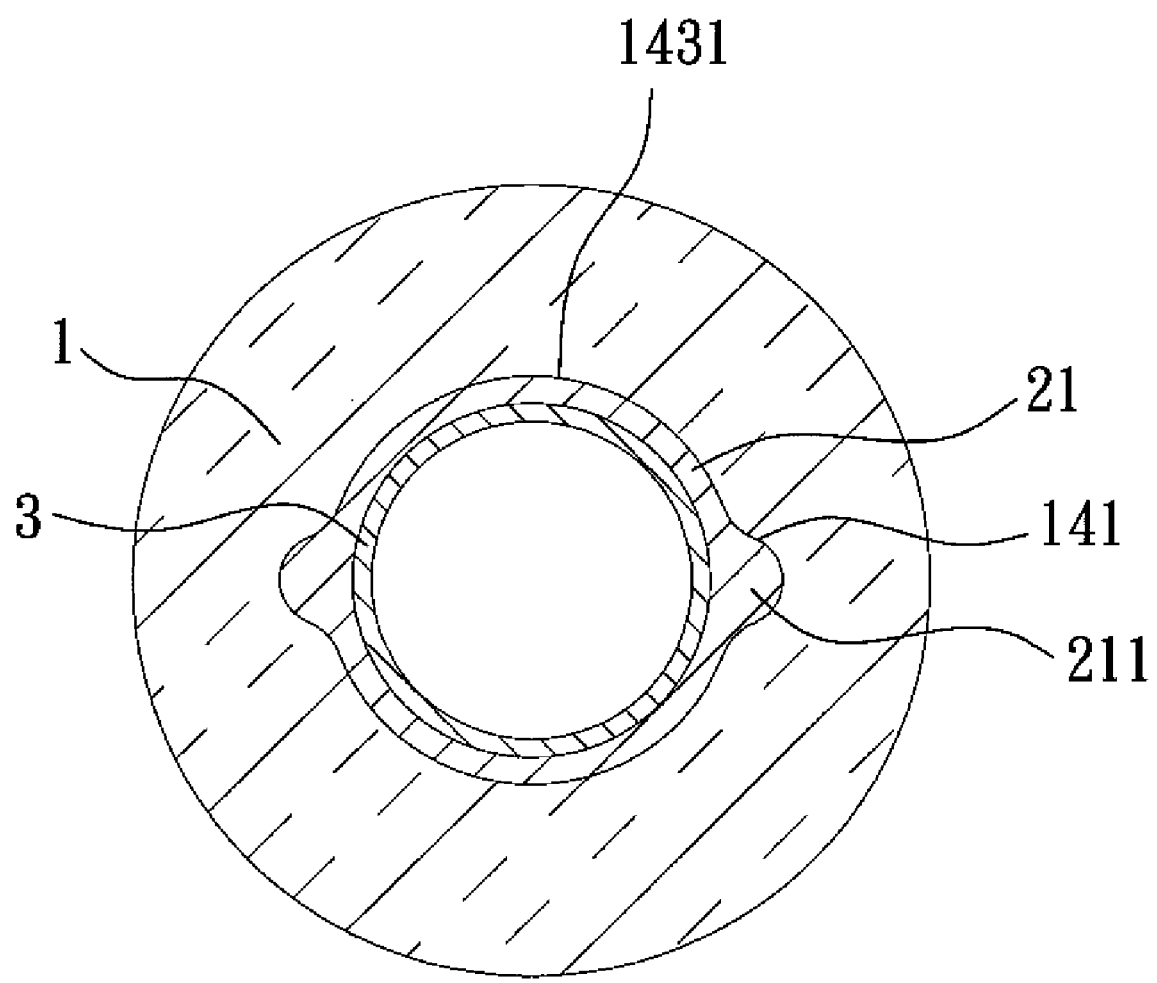
FIG. 4 is cross-sectional view taken along lines 4-4 of FIG. 3(A)

Before the present invention is described in greater detail, it should be noted that same reference numerals have been used to denote like elements throughout the specification.

Figure 5:
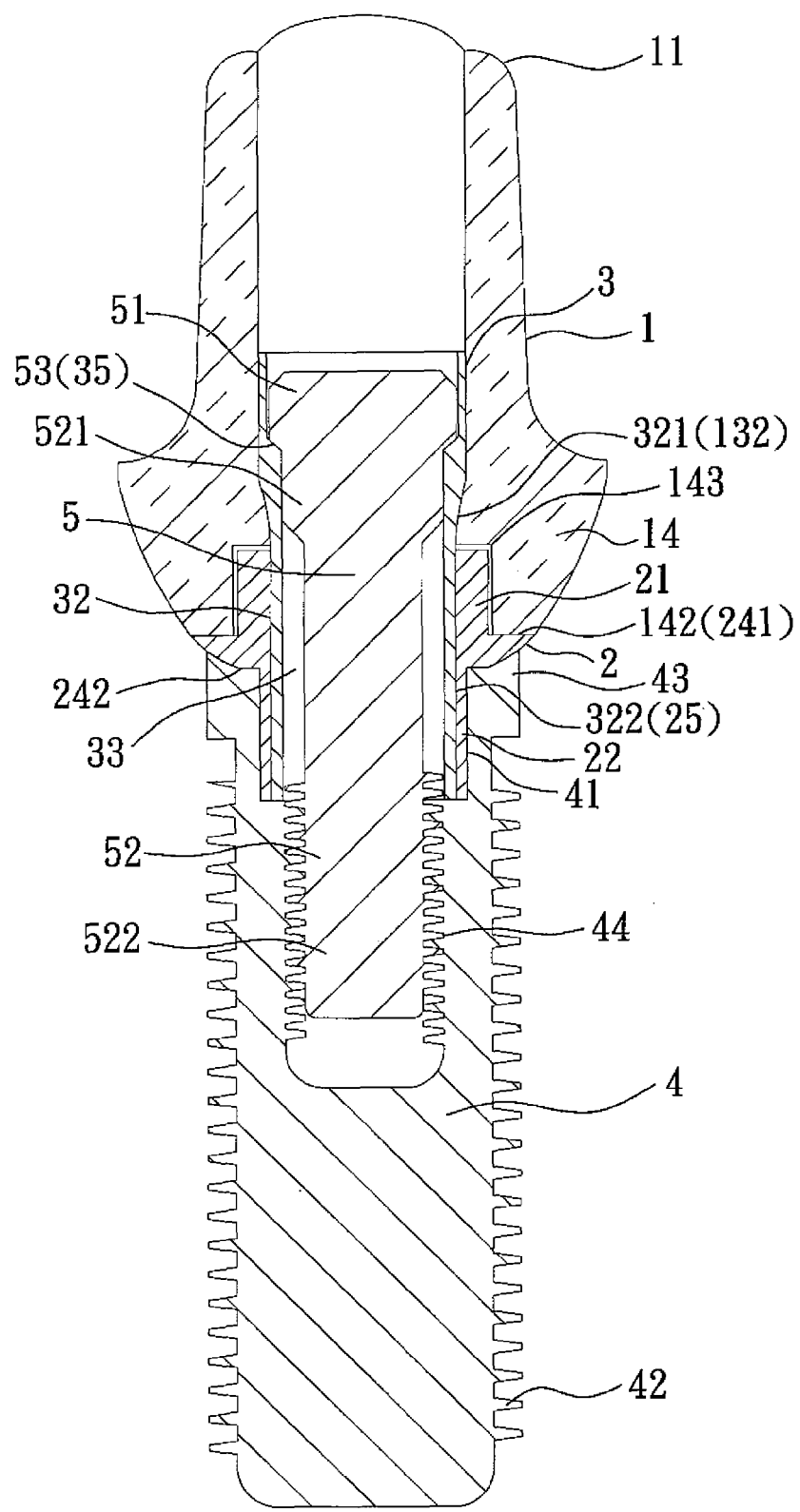
FIG. 5 is a sectional view of the first preferred embodiment when incorporated with a dental implant unit.

Referring to FIG. 5, the first preferred embodiment of an abutment assembly according to the present invention is adapted for use with a dental implant unit which includes an implant member 4 and a bolt member 5. The implant member 4 includes an osseous end 42 that is screwable into a jaw bone of a patient, a gingival end 43 disposed opposite to the osseous end 42 in a longitudinal direction, and tubular threaded and fitted walls 44,41 which are respectively distal from and proximate to the gingival end 43. The tubular fitted wall 41 is formed as an interface. The bolt member 5 includes an enlarged head 51 and a shank 52 which has a proximate segment 521 that cooperates with the enlarged head 51 to form a force-applying shoulder 53 between the head 51 and the shank 52, and a distal segment 522 that is disposed to threadedly engage the tubular threaded wall 44 so as to move the force-applying shoulder 53 towards the gingival end 43.

With reference to FIGS. 1 to 4, the abutment assembly is shown to comprise a pedestal unit 2, an abutment body 1, and a tubular packing member 3, each of which is of a one-single-piece construction.

The pedestal unit 2 is made from a metal material, and includes a surrounding mount 24, a tubular post 21, and a fitting bushing 22. The surrounding mount 24 has an upper mount surface 241 and a lower mount surface 242 that is opposite to the upper mount surface 241 in the longitudinal direction, and that is adapted to rest on the gingival end 43 of the implant member 4. The tubular post 21 extends from the upper mount surface 241 upwardly to terminate at a tubular seat surface 212, and cooperates with the surrounding mount 24 to define an inner tubular abutted surface 25 that is adapted to surround the proximate segment 521 of the bolt member 5. The fitting bushing 22 extends from the lower mount surface 242 downwardly to form an interface. The fitting bushing 22 is adapted to extend into the tubular fitted wall 41 of the implant member 4, and has a polyhedral cross-section so as to be in non-rotatable engagement with the tubular fitted wall 41 of the implant member 4.

The abutment body 1 is made from a ceramic material, and includes coping-side and bottom walls 11,14 opposite to each other in the longitudinal direction. The abutment body 1 has an inner tubular wall surface 13 which extends longitudinally through the coping-sidewall 11 and the bottom wall 14 to form a tubular passage region 131 and a tubular pressed region 132 that are proximate to the coping-side wall 11 and the bottom wall 14, respectively. The bottom wall 14 has an annular cut-out 143 which extends longitudinally into the tubular pressed region 132, and which extends inwardly and radially through the inner tubular wall surface 13 so as to form a surrounding shoulder abutment 15 that confronts the tubular seat surface 212 of the tubular post 21 in the longitudinal direction. The annular cut-out 143 extends longitudinally into the tubular pressed region 132 to form an inner surrounding shielding surface 1431, which is in splined engagement with the tubular post 21. In this embodiment, two longitudinal grooves 141 are formed in the inner surrounding shielding surface 1431 and are diametrically opposite to each other, and two ridges 211 are formed on the tubular post 21 to be inserted into the longitudinal grooves 141, respectively, so as to guard against rotation of the abutment body 1 relative to the pedestal unit 2. Additionally, the bottom wall 14 extends in radial directions and outwardly to terminate at an outer peripheral edge 142, which abuts against the upper mount surface 241 of the surrounding mount 24 so as to guard against upward movement of the pedestal unit 2 towards the coping-side wall 11.

The tubular packing member 3 has an inner peripheral surface 34 extending longitudinally to define a through bore 33, and an outer peripheral surface 32 opposite to the inner peripheral surface 34 in radial directions. The inner peripheral surface 34 includes a proximate peripheral regions 341 which is adapted to provide access to the bolt member 5, and a distal peripheral region 342 which extends downwardly from the proximate peripheral region 341, and which is configured to form, in cooperation with the proximate peripheral region 341, a bearing ledge 35 that confronts the force-applying shoulder 53 of the bolt member 5 when the distal segment 522 of the bolt member 5 is brought to threadedly engage the tubular threaded wall 44 of the implant member 4.

The outer peripheral surface 32 of the tubular packing member 3 includes pressing and abutting regions 321,322 which are proximate to and distal from the bearing ledge 35, respectively, and which are configured to mate with the tubular pressed region 132 and the inner tubular abutted surface 25, respectively. Thus, once the bearing ledge 35 is forced by the force-applying shoulder 53, by virtue of screwing of the distal segment 522 in the tubular threaded wall 44, to place the abutment body 1 in a tightened position, the pressing and abutting regions 321,322 are brought to intimately abut against the tubular pressed region 132 and the inner tubular abutted surface 25, respectively, to thereby ensure immobility of the abutment body 1 relative to the bolt member 5.

In assembly, as shown in FIG. 5, the fitting bushing 22 (i.e., the interface) of the pedestal unit 2 is first inserted into the tubular fitted wall 41 (i.e., the interface) of the implant member 4 to permit the lower mount surface 242 to rest on the gingival end 43. Subsequently, the annular cut-out 143 of the abutment body 1 is engaged with the tubular post 21 of the pedestal unit 2 to permit the outer peripheral edge 142 to abut against the upper mount surface 241. Then, the tubular packing member 3 is inserted into the inner tubular wall surface 13 from the tubular passage region 131 such that the pressing and abutting regions 321,322 are matingly engaged with the tubular pressed region 132 and the inner tubular abutted surface 25, respectively. Thereafter, the bolt member 5 is inserted into the through bore 33 to permit the distal segment 522 to threadedly engage the tubular threaded wall 44 so as to place the abutment body 1 in the tightened position as described above. Finally, the bolt member 5 is screwed out and the abutment assembly is removed from the implant member 4.

As illustrated, since the abutment body 1 is made from a ceramic material, the appearance of an artificial tooth or crown which is mounted on the abutment body 1 is improved. Additionally, by virtue of the metal-made pedestal unit 2 which can be connected to the metal-made implant member 4, the connection between the implant member 4 and the abutment assembly can be reliably ensured and easy to establish, and breaking at the connection can be avoided. Further, since the ceramic-made abutment body 1 is separated from the metal-made implant member 4 by the pedestal unit 2, possible damage to the implant member 4 during mounting and position-adjustment of the abutment assembly on the implant member 4 can be prevented. It is noted that the pedestal unit 2 is easy to replace if damaged.

Figure 6:
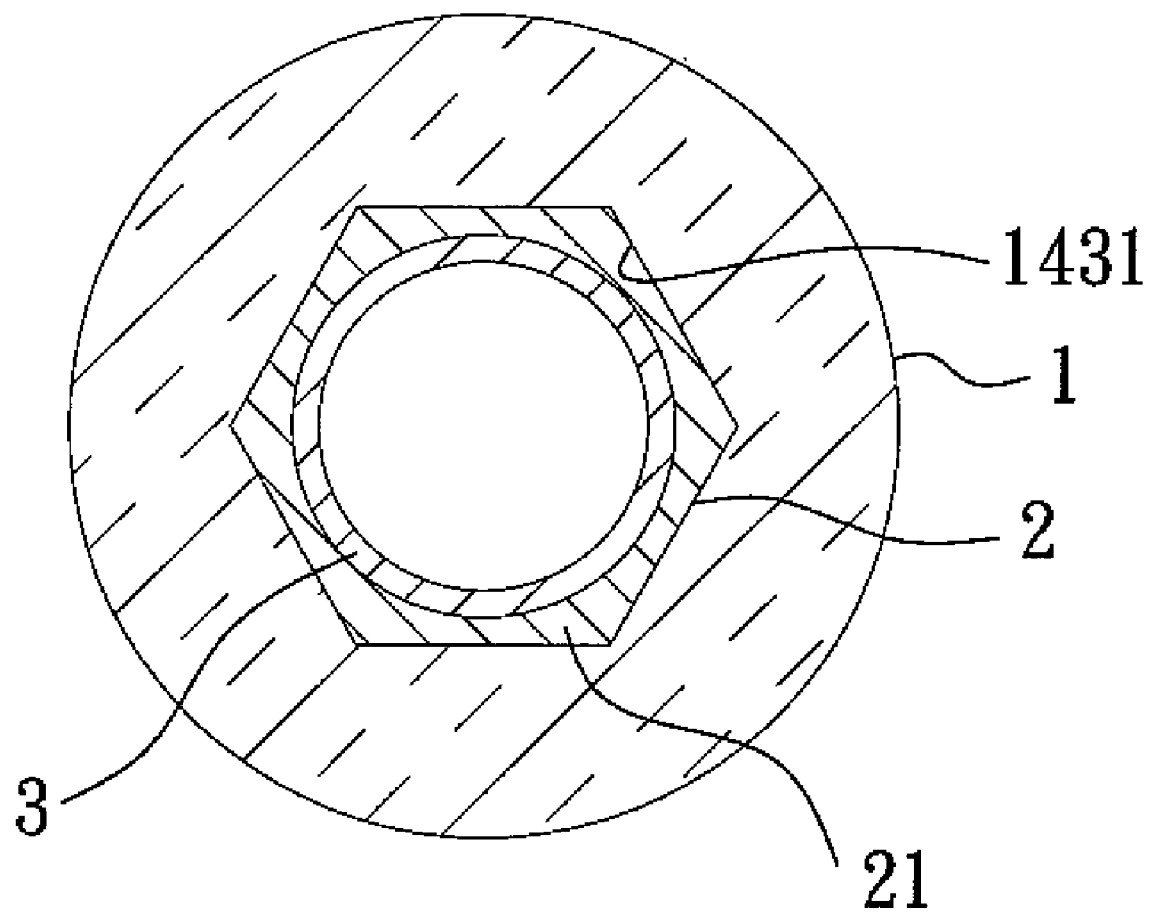
FIG. 6 is a cross-sectional view of the second preferred embodiment of an abutment assembly according to this invention.

Referring to FIG. 6, the second preferred embodiment of an abutment assembly according to this invention is shown to be similar to the first preferred embodiment. In this embodiment, the tubular post 21 and the inner surrounding shielding surface 1431 have complementary polygonal cross-sections, e.g., hexagonal cross-sections, so as to permit splined engagement between the abutment body 1 and the pedestal unit 2.

Figure 7A:
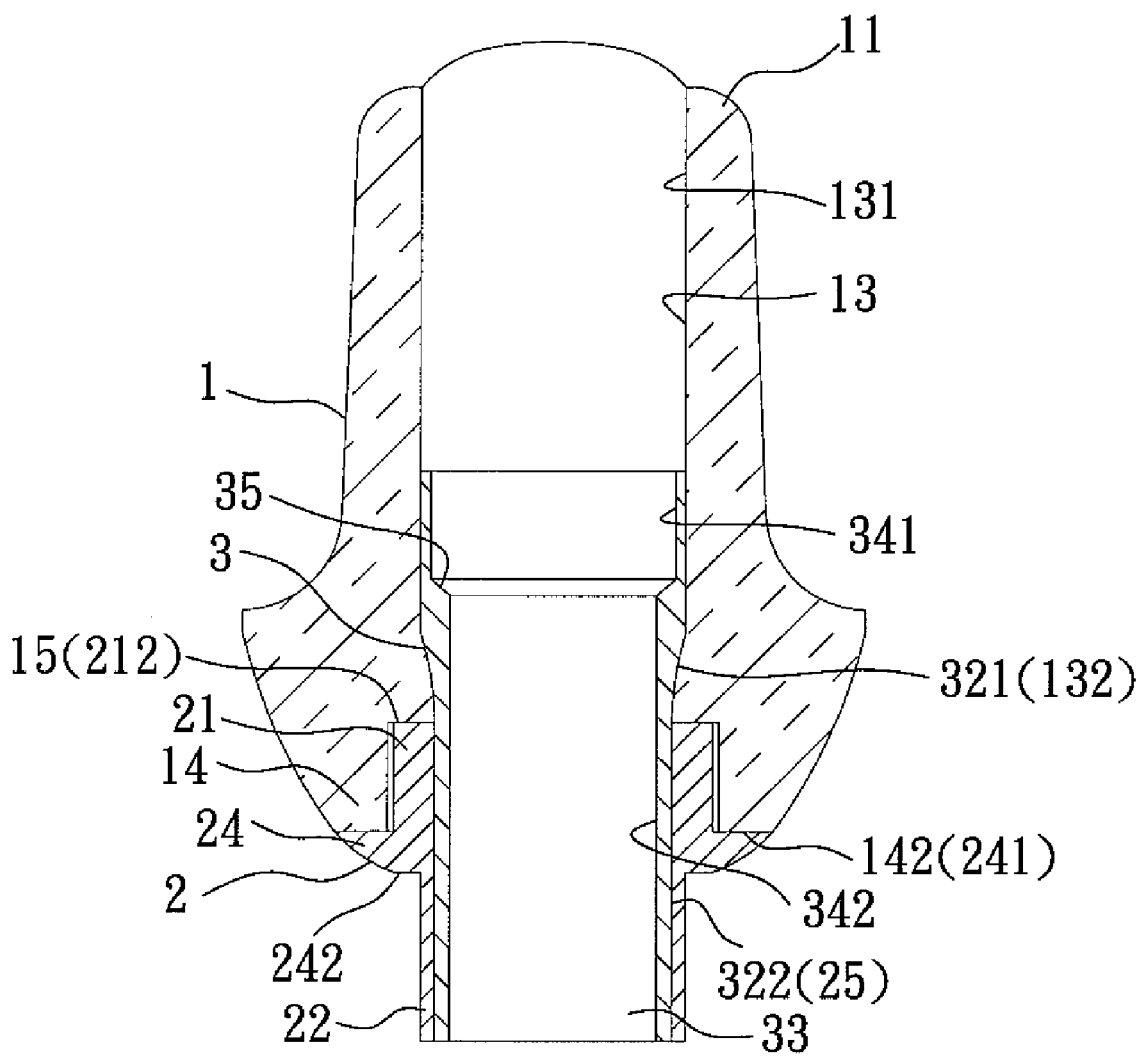
FIG. 7(A) is a sectional view of the third preferred embodiment of an abutment assembly according to this invention when assembled.
Figure 7B:
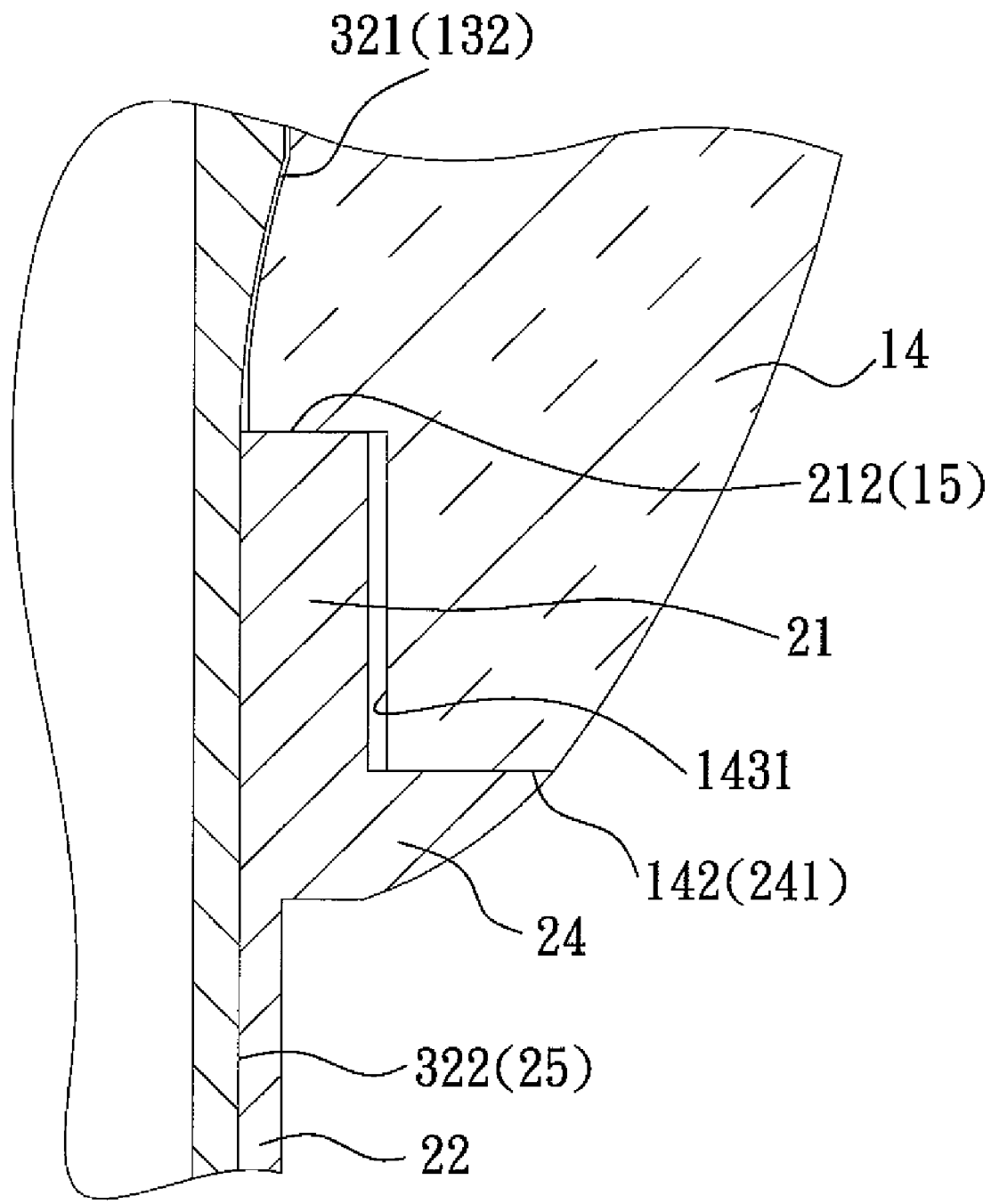
FIG. 7(B) is an enlarged view of a portion in FIG. 7(A)

Referring to FIGS. 7(A) and 7(B), the third preferred embodiment of an abutment assembly according to this invention is shown to be similar to the first preferred embodiment. In the third embodiment, the surrounding shoulder abutment 15 of the bottom wall 14 of the abutment body 1 is disposed to abut against the tubular seat surface 212 of the tubular post 21 of the pedestal unit 2 so as to guard against upward movement of the pedestal unit 2 relative to the abutment body 1.

Figure 8:
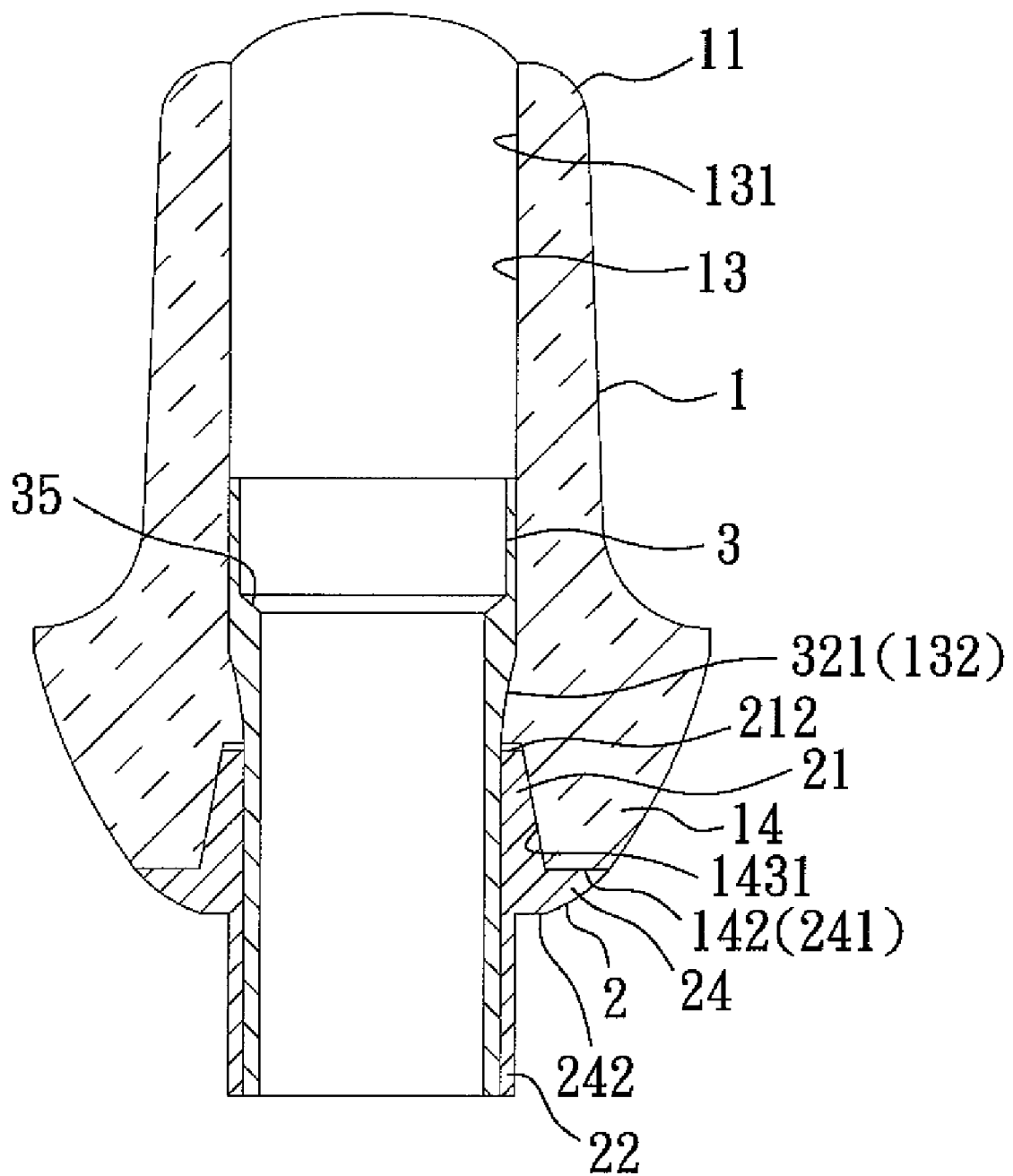
FIG. 8 is a sectional view of the fourth preferred embodiment of an abutment assembly according to this invention when assembled.

Referring to FIG. 8, the fourth preferred embodiment of an abutment assembly according to this invention is shown to be similar to the first preferred embodiment. In the fourth embodiment, the tubular post 21 of the pedestal unit 2 is configured to converge toward the tubular seat surface 212 to acquire a frusto-conical shape, and the inner surrounding shielding surface 143 of the bottom wall 14 of the abutment body 1 has a frusto-conical shape so as to matingly engage the tubular post 21 to thereby guard against upward movement of the pedestal unit 2 relative to the abutment body 1.

Figure 9:
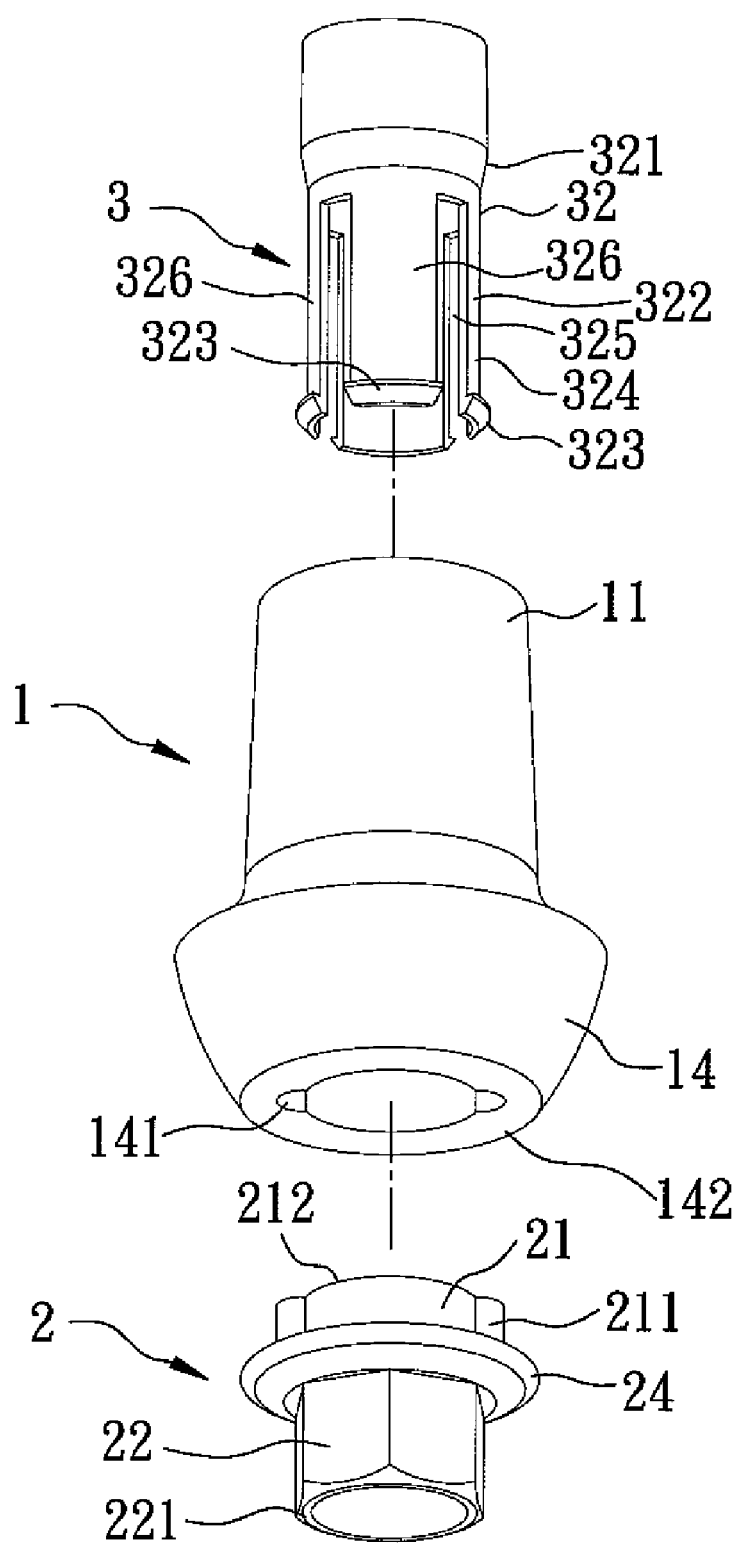
FIG. 9 is an exploded perspective view of the fifth preferred embodiment of an abutment assembly according to this invention.
Figure 10:
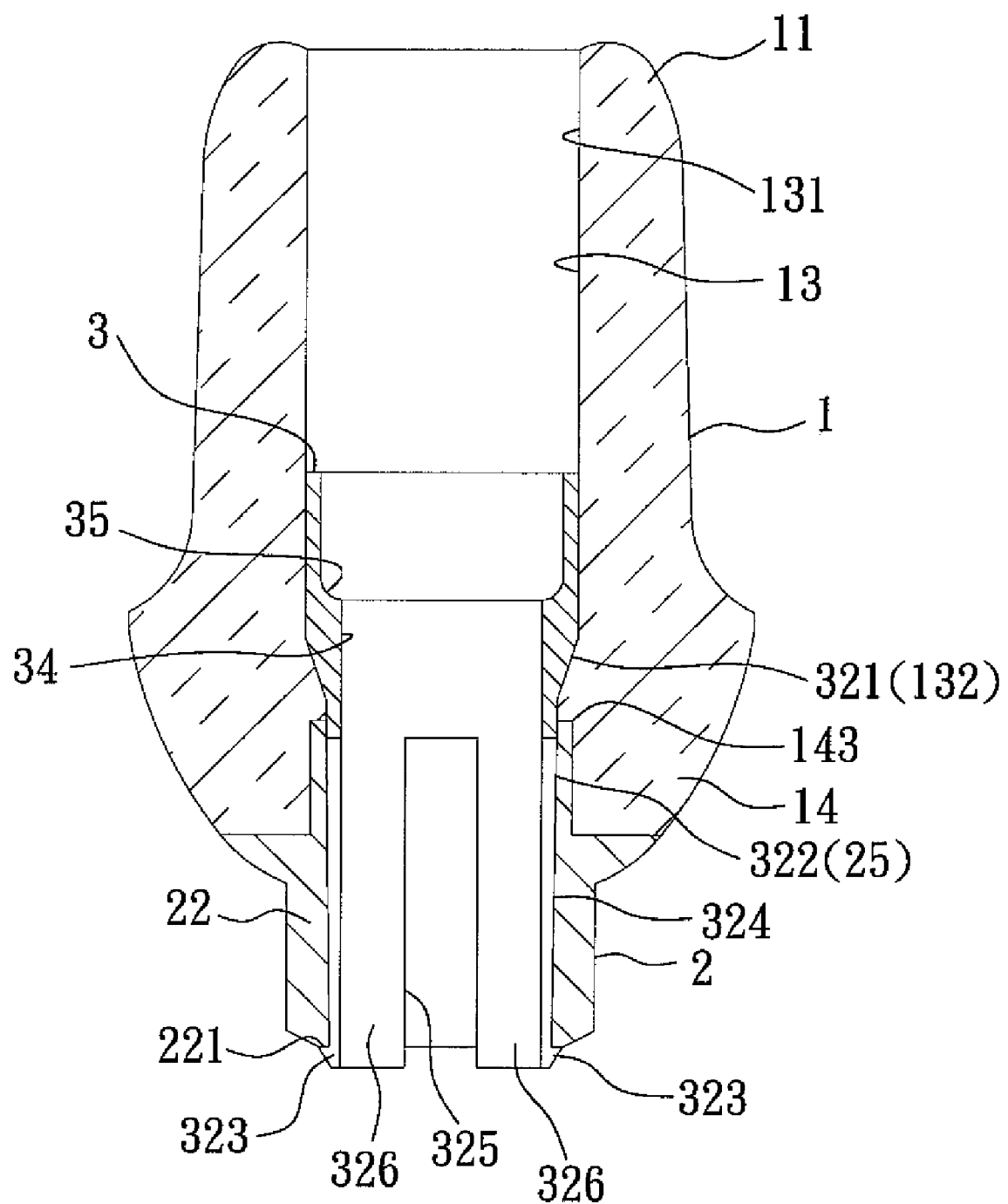
FIG. 10 is a sectional view of the fifth preferred embodiment when assembled.

Referring to FIGS. 9 and 10, the fifth preferred embodiment of an abutment assembly according to this invention is shown to be similar to the first preferred embodiment. In the fifth embodiment, the outer peripheral surface 32 of the tubular packing member 3 has a leading region 324 which extends downwardly from the abutting region 322 to be disposed in the tubular fitted wall 41 of the implant member 4 (see FIG. 5) so as to help hold the fitting bushing 22 in non-rotatable engagement with the tubular fitted wall 41. The leading region 324 has a plurality of longitudinal slits 325 which extend through the inner peripheral surface 34 and in the longitudinal direction, and which are angularly displaced from one another so as to divide the leading region 324 into a plurality of resilient segments 326. Each of the resilient segments 326 has a flange 323 opposite to the bearing ledge 35 in the longitudinal direction such that, when the leading region 324 is inserted into the inner tubular abutted surface 25 from the tubular passage region 131, the resilient segments 326 are deformed by the inner tubular abutted surface 25, thereby acquiring a biasing force. The biasing force biases the flanges 323 to extend radially and outwardly such that the flanges 323 are snapped into engagement with a bottom edge 221 of the fitting bushing 22 to be thereby retained.

Figure 11:
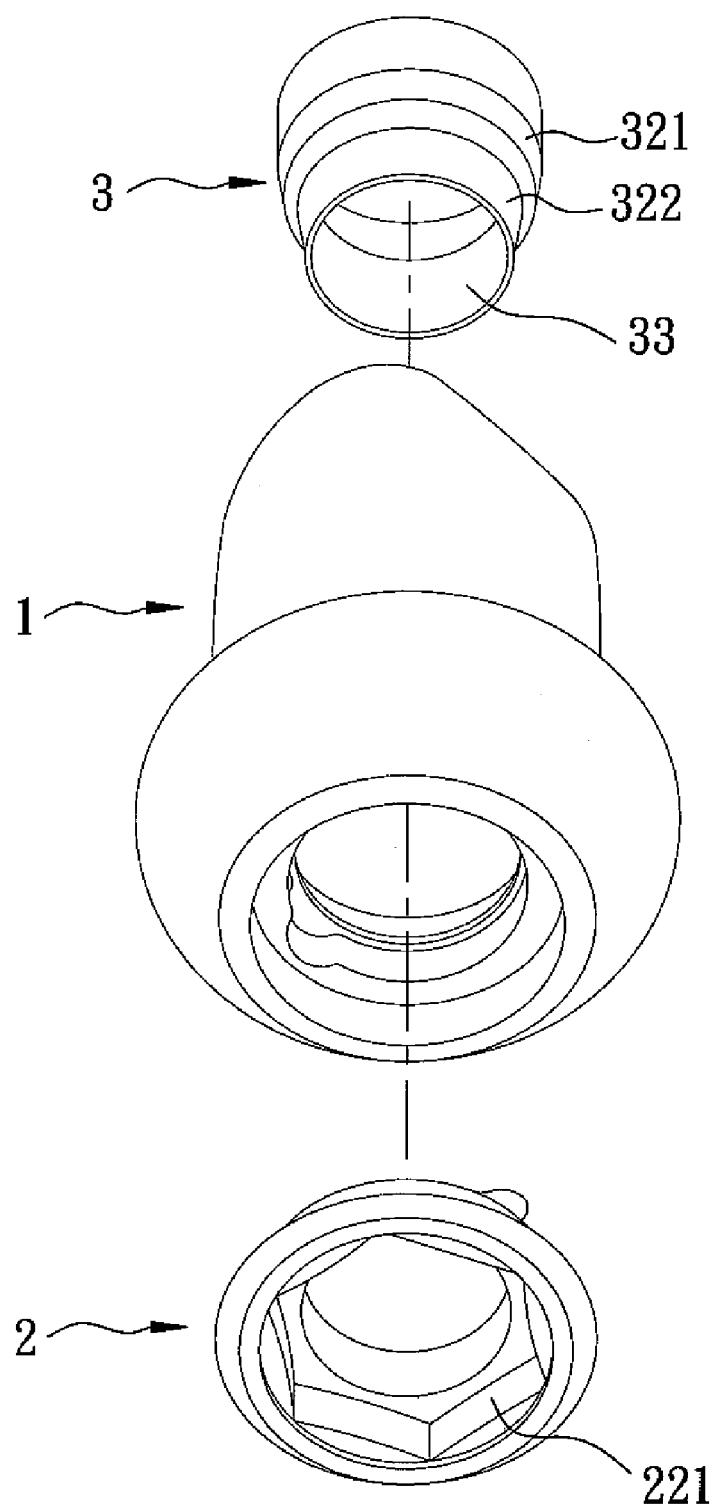
FIG. 11 is an exploded perspective view of the sixth preferred embodiment of an abutment assembly according to this invention.
Figure 12:
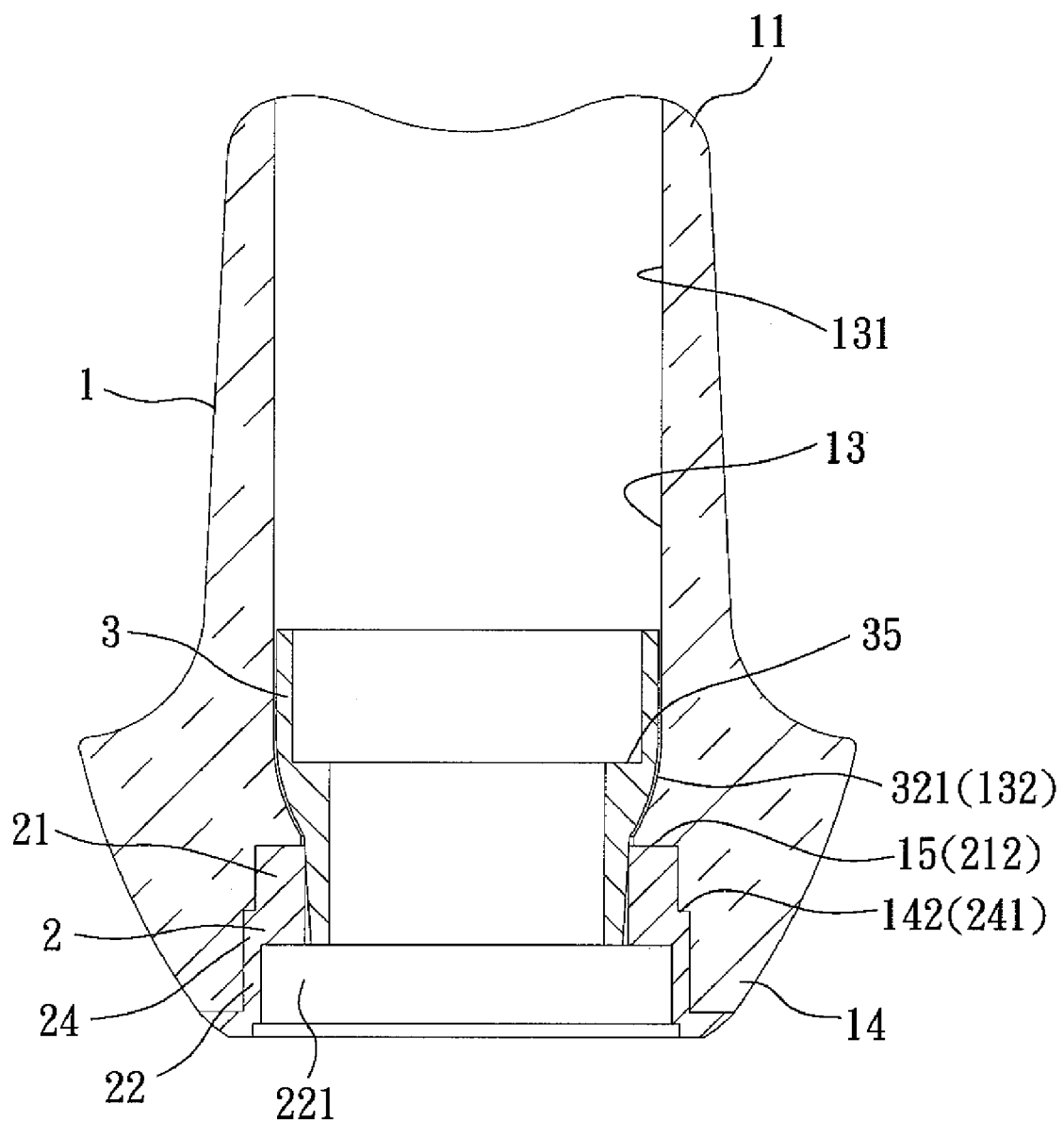
FIG. 12 is a sectional view of the sixth preferred embodiment when assembled.

Referring to FIGS. 11 and 12, the sixth preferred embodiment of an abutment assembly according to this invention is shown to be similar to the first preferred embodiment. In the sixth embodiment, the fitting bushing 22 of the pedestal unit 2 has a polyhedral fitting hole 221 to be in non-rotatable engagement with the tubular fitted wall 41 of the implant member 4 (see FIG. 5).

While the present invention has been described in connection with what are considered the most practical and preferred embodiments, it is understood that this invention is not limited to the disclosed embodiments but is intended to cover various arrangements included within the spirit and scope of the broadest interpretations and equivalent arrangements.

We claim:

1. An abutment assembly for use with a dental implant unit which includes an implant member and a bolt member, the implant member including an osseous end screwable into a jawbone of a patient, a gingival end disposed opposite to the osseous end in a longitudinal direction, and tubular threaded and fitted walls which are respectively distal from and proximate to the gingival end, the bolt member including an enlarged head and a shank which has a proximate segment that cooperates with the enlarged head to form a force-applying shoulder between the head and the shank, and a distal segment that is disposed to threadedly engage the tubular threaded wall so as to move the force-applying shoulder towards the gingival end, said abutment assembly comprising:

a pedestal unit including:
  a surrounding mount which has an upper mount surface and a lower mount surface that is opposite to said upper mount surface in the longitudinal direction, and that is adapted to rest on the gingival end;
  a tubular post which extends from said upper mount surface upwardly to terminate at a tubular seat surface, and which, in cooperation with said surrounding mount, defines an inner tubular abutted surface that is adapted to surround the proximate segment; and
  a fitting bushing which extends from said lower mount surface downwardly, and which is adapted to be in fitting engagement with the tubular fitted wall;

an abutment body including coping-side and bottom walls opposite to each other in the longitudinal direction, and having an inner tubular wall surface which extends longitudinally through said coping-side wall and said bottom wall to form a tubular passage region and a tubular pressed region that are proximate to said coping-side wall and said bottom wall, respectively, said bottom wall having an annular cut-out which extends longitudinally into said tubular pressed region, and which extends inwardly and radially through said inner tubular wall surface so as to form a surrounding shoulder abutment that confronts said tubular seat surface in the longitudinal direction; and a tubular packing member having:
  an inner peripheral surface extending longitudinally to define a through bore, and including a proximate peripheral region which is adapted to provide access to the bolt member, and a distal peripheral region which extends downwardly from said proximate peripheral region, and which is configured to form, in cooperation with said proximate peripheral region, a bearing ledge that confronts the force-applying shoulder when the distal segment is brought to threadedly engage said tubular threaded wall; and
  an outer peripheral surface opposite to said inner peripheral surface in radial directions, said outer peripheral surface including pressing and abutting regions which are proximate to and distal from said bearing ledge, respectively, and which are configured to mate with said tubular pressed region and said inner tubular abutted surface, respectively, such that, once said bearing ledge is forced by the force-applying shoulder, by virtue of screwing of the distal segment in the tubular threaded wall, to place said abutment body in a tightened position, said pressing region is brought to intimately abut against said tubular pressed region to thereby ensure immobility of said abutment body relative to the bolt member.

2. The abutment assembly according to claim 1, wherein said abutting region of said outer peripheral surface is disposed to intimately abut against said inner tubular abutted surface once said bearing ledge is forced by the force-applying shoulder to place said abutment body in the tightened position.

3. The abutment assembly according to claim 1, wherein each of said pedestal unit, said abutment body and said tubular packing member is of a one-single-piece construction, said pedestal unit being made from a metal material.

4. The abutment assembly according to claim 1, wherein said annular cut-out extends longitudinally into said tubular pressed region to form an inner surrounding shielding surface which is in splined engagement with said tubular post so as to guard against rotation of said abutment body relative to said pedestal unit.

5. The abutment assembly according to claim 4, wherein each of said tubular post and said inner surrounding shielding surface has a non-circular cross-section.

6. The abutment assembly according to claim 4, wherein said tubular post is configured to converge toward said tubular seat surface to thereby acquire a frusto-conical shape.

7. The abutment assembly according to claim 1, wherein said bottom wall of said abutment body extends radially and outwardly to terminate at an outer peripheral edge which abuts against said upper mount surface of said surrounding mount so as to guard against upward movement of said pedestal unit towards said coping-side wall.

8. The abutment assembly according to claim 1, wherein said fitting bushing of said pedestal unit is adapted to extend into the tubular fitted wall of the implant member, and has a polyhedral cross-section so as to be in non-rotatable engagement with the tubular fitted wall.

9. The abutment assembly according to claim 8, wherein said outer peripheral surface of said tubular packing member has a leading region which extends downwardly from said abutting region to be disposed in the tubular fitted wall of the implant member so as to help hold said fitting bushing in non-rotatable engagement with the tubular fitted wall, said leading region having a plurality of longitudinal slits which extend through said inner peripheral surface and in the longitudinal direction, and which are angularly displaced from one another so as to divide said leading region into a plurality of resilient segments, each of said resilient segments having a flange opposite to said bearing ledge in the longitudinal direction such that, when said leading region is inserted into said inner tubular abutted surface from said tubular passage region, said resilient segments are deformed by said inner tubular abutted surface to thereby acquire a biasing force so as to bias said flanges to extend radially and outwardly such that said flanges are snapped into engagement with a bottom edge of said fitting bushing to be thereby retained.

10. The abutment assembly according to claim 1, wherein said surrounding shoulder abutment of said bottom wall is disposed to abut against said tubular seat surface of said tubular post.

11. The abutment assembly according to claim 1, wherein said fitting bushing has a polyhedral fitting hole which is adapted to be in non-rotatable engagement with the tubular fitted wall.

\* \* \* \* \*